(12) United States Patent
Govind et al.

(10) Patent No.: US 8,575,137 B2
(45) Date of Patent: *Nov. 5, 2013

(54) COMPOSITION FOR INHALATION

(75) Inventors: Nayna Govind, Loughborough (GB); Maria Marlow, Loughborough (GB)

(73) Assignee: AstraZeneca AB, Macclesfield (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/411,939

(22) Filed: Mar. 5, 2012

(65) Prior Publication Data
US 2012/0216802 A1  Aug. 30, 2012

Related U.S. Application Data

(63) Continuation of application No. 12/790,196, filed on May 28, 2010, now Pat. No. 8,143,239, and a continuation of application No. 10/502,685, filed as application No. PCT/SE03/00156 on Jan. 29, 2003, now Pat. No. 7,759,328.

(30) Foreign Application Priority Data

Feb. 1, 2002 (SE) ...................... 0200312

(51) Int. Cl.
*A01N 45/00* (2006.01)
*A61K 31/335* (2006.01)

(52) U.S. Cl.
USPC ......................................... 514/167; 514/463

(58) Field of Classification Search
None
See application file for complete search history.

(56) References Cited

U.S. PATENT DOCUMENTS

| | | | |
|---|---|---|---|
| 6,004,537 A | 12/1999 | Blondino et al. | |
| 6,123,924 A | 9/2000 | Mistry et al. | |
| 6,309,623 B1 | 10/2001 | Weers et al. | |
| 7,759,328 B2 * | 7/2010 | Govind et al. | 514/167 |
| 8,143,239 B2 * | 3/2012 | Govind et al. | 514/167 |
| 2003/0018019 A1 | 1/2003 | Meade et al. | |
| 2010/0275913 A1 | 11/2010 | Govind et al. | |

FOREIGN PATENT DOCUMENTS

| | | |
|---|---|---|
| CA | 2338753 | 2/2000 |
| EP | 0534731 | 3/1993 |
| WO | WO 93/05765 | 4/1993 |
| WO | WO 93/11773 | 6/1993 |
| WO | WO 98/15280 | 4/1998 |
| WO | WO 98/21175 | 5/1998 |
| WO | WO 99/15182 | 4/1999 |
| WO | WO 99/64014 | 12/1999 |
| WO | WO 00/53188 | 9/2000 |
| WO | WO 01/78693 | 10/2001 |
| WO | WO 01/78737 | 10/2001 |
| WO | WO 01/89492 | 11/2001 |
| WO | WO 02/03958 | 1/2002 |

OTHER PUBLICATIONS

Brindley, "The chlorofluorocarbon to hydrofluoroalkane transition: The effect on pressurized metered dose inhaler suspension stability," J. Allergy Clin. Immunol., vol. 104, pp. s221-s226 (1999).
Byron, "Respiratory Drug Delivery," CRC Press, Inc., pp. 185-201 (1990).
Calverley et al., "Maintenance therapy with budesonide and formoterol in chronic obstructive pulmonary disease", Eur. Respir. J., vol. 22, pp. 912-919 (2003).
Cazzola et al., "Effect of salmeterol and formoterol in patients with chronic obstructive pulmonary disease," Pulm. Pharmacol. vol. 7, pp. 103-107 (1994).
Communication of a Notice of Opposition against Patent No. EP1474117 from the European Patent Office, dated Dec. 4, 2009 (27 pages).
Jinks, "A rapid technique for characterisation of the suspension dynamics of metered dose inhaler formulations," Proceedings of Drug Delivery to the Lungs VI, London: The Aerosol Society, 1995; Abstract supplied by The British Library (2 pages).
Lumry, "A review of the preclinical and clinical data of newer intranasal steroids used in the treatment of allergic rhinitis," J. Allergy Clin. Immunol. 1, vol. 4, pp. S150-S158 (1999) (abstract only).
Milgrom and Taussig, "Keeping Children with Exercise-Induced Asthma Active," Pediatrics, vol. 104, pp. 38-42 (1999).
Pauwels et al., "Effect of inhaled formoterol and budesonide on exacerbations of asthma," vol. 337, No. 20, pp. 1405-1411 (and one correction page), Nov. 13, 1997.
Pipkorn et al., "Budesonide—a New Nasal Steroid," Rhinology, vol. 18, pp. 171-175 (1980).
"Povidone," The United States Pharmacopeia, USP25/NF20, pp. 1419-1420, United States Pharmacopeial Convention, Inc., Rockville, MD (2002).
Renkema et al., "Effects of long-term treatment with corticosteroids in COPD," Chest, vol. 109, pp. 1156-1162 (1996).
TurbiScan MA 2000 brochure (6 pages) (2000).
Turbiscan MA 2000, Sci-Tec Inc., [online] Retrieved from http://www.sci-tec-inc.com/Turbiscan%20Classic%20MA%20200.html, Retrieved on Oct. 20, 2009 (3 pages).
Vippagunta et al. "Crystalline Solids," Advanced Drug Delivery Reviews, vol. 48, p. 18 (2001).
Wyser et al., "Neue Aspekte in der Behandlung des Asthma bronchiale und chronisch obstruktiver Lundenkrankeiten," Schweiz Med. Wochenschr, vol. 127, pp. 885-890 (1997), English Summary Included.
Zetterström et al., "Improved asthma control with budesonide/formoterol in a single inhaler, compared with budesonide alone," Eur. Respir. J., vol. 18, pp. 262-268 (2001).
Office Action, in U.S. Appl. No. 10/502,685, mailed May 4, 2006 (12 pages).
Fish & Richardson P.C., Reply to Office Action in U.S. Appl. No. 10/502,685 mailed May 4, 2006, filed Nov. 3, 2006 (12 pages).
Fish & Richardson P.C., Submission Under 37 CFR § 1.114(c) in U.S. Appl. No. 10/502,685, filed Aug. 21, 2007 (12 pages).
Office Action in U.S. Appl. No. 10/502,685, mailed Jan. 31, 2008 (4 pages).

(Continued)

*Primary Examiner* — Alton Pryor
(74) *Attorney, Agent, or Firm* — Fish & Richardson P.C.

(57) ABSTRACT

The invention relates to a formulation comprising formoterol and budesonide for use in the treatment of respiratory diseases. The composition further contains HFA 227, PVP and PEG, preferably PVP K25 and PEG 1000.

53 Claims, 16 Drawing Sheets

(56) References Cited

OTHER PUBLICATIONS

Fish & Richardson P.C., Reply to Office Action in U.S. Appl. No. 10/502,685 mailed Jan. 31, 2008, filed Apr. 30, 2008 (10 pages).
Office Action in U.S. Appl. No. 10/502,685, mailed Aug. 1, 2008 (26 pages).
Fish & Richardson P.C., Reply to Office Action in U.S. Appl. No. 10/502,685 mailed Aug. 1, 2008, filed Oct. 31, 2008 (9 pages).
Office Action in U.S. Appl. No. 10/502,685, mailed Jan. 27, 2009 (11 pages).
Fish & Richardson P.C., Amendment in Reply to Office Action in U.S. Appl. No. 10/502,685 mailed Jan. 27, 2009, filed May 26, 2009 (8 pages).
Fish & Richardson P.C., Supplemental Amendment in U.S. Appl. No. 10/502,685, filed Aug. 21, 2009 (5 pages).
Fish & Richardson P.C., Amendment in U.S. Appl. No. 10/502,685, filed Nov. 12, 2009 (9 pages).
Fish & Richardson P.C., Communication Pursuant to 37 C.F.R. §1.312 in U.S. Appl. No. 10/502,685, filed Mar. 15, 2010 (3 pages).
Fish & Richardson P.C., Preliminary Amendment and Interview Summary in U.S. Appl. No. 12/790,196, filed Nov. 1, 2010 (8 pages).
Office Action in U.S. Appl. No. 12/790,196, mailed May 25, 2011 (11 pages).
Fish & Richardson P.C., Amendment in Reply to Office Action in U.S. Appl. No. 12/790,196 mailed May 25, 2011, filed Oct. 17, 2011 (8 pages).
Fish & Richardson P.C., Amendment After Allowance in U.S. Appl. No. 12/790,196, filed Nov. 22, 2011 (8 pages).

* cited by examiner

PEG concn = left – right 0.005, 0.05, 0.35 and 0.5% w/w

COMPOSITION FOR INHALATION

CROSS-REFERENCE TO RELATED APPLICATIONS

This application is a continuation of U.S. application Ser. No. 12/790,196, filed May 28, 2010, which is a continuation of U.S. application Ser. No. 10/502,685, filed Jul. 27, 2004, now issued as U.S. Pat. No. 7,759,328, which is a national phase application under 35 U.S.C. §371 of PCT International Application No. PCT/SE2003/000156, filed Jan. 29, 2003, which claims priority to Swedish Application Serial No. 0200312-7, filed Feb. 1, 2002. The contents of these prior applications are incorporated herein by reference in their entirety.

TECHNICAL FIELD

The present invention relates to a formulation comprising formoterol and budesonide for use in the treatment of inflammatory conditions/disorders, especially respiratory diseases such as asthma, COPD and rhinitis.

BACKGROUND

Stability is one of the most important factors which determines whether a compound or a mixture of compounds can be developed into a therapeutically useful pharmaceutical product.

Combinations of formoterol and budesonide are known in the art, see for example WO 93/11773 discloses such a combination that is now marketed as Symbicort® in a dry powder inhaler. There are a variety of other inhalers by which a respiratory product can be administered, such as pressurised metered dose inhalers (pMDI's). Formulations for pMDI's may require certain excipients as disclosed in WO 93/05765.

It has now been found that certain HFA formulations comprising formoterol and budesonide together with polyvinylpyrrolidone (PVP) and polyethylene glycol (PEG) exhibit excellent physical suspension stability.

Description

In accordance with the present invention, there is provided a pharmaceutical composition comprising formoterol, budesonide, HFA 227 (1,1,1,2,3,3,3-heptafluoropropane), PVP and PEG characterised in that the PVP is present from about 0.0005 to about 0.03% w/w and the PEG is present from about 0.05 to about 0.35% w/w.

Preferably the PVP is present in an amount of 0.001% w/w. Preferably the PVP is PVP K25 (PVP having a nominal K-value of 25).

Preferably the PEG is present in an amount of 0.3% w/w. Preferably the PEG is PEG 1000 (PEG having an average molecular weight of 1000 Daltons).

Preferably the concentrations of formoterol/budesonide are such that the formulation delivers formoterol/budesonide at 4.5/40 mcg, 4.5/80 mcg, 4.5/160 mcg or 4.5/320mcg per actuation.

The formoterol can be in the form of a mixture of enantiomers. Preferably the formoterol is in the form of a single enantiomer, preferably the R,R enantiomer. The formoterol can be in the form of the free base, salt or solvate, or a solvate of a salt, preferably the formoterol is in the form of its fumarate dihydrate salt. Other suitable physiologically salts that can be used include chloride, bromide, sulphate, phosphate, maleate, tartrate, citrate, benzoate, 4-methoxybenzoate, 2- or 4-hydroxybenzoate, 4-chlorobenzoate, p-toluenesulphonate, benzenesulphonate, ascorbate, acetate, succinate, lactate, glutarate, gluconate, tricaballate, hydroxynapaphthalenecarboxylate or oleate. Preferably the second active ingredient is budesonide, including epimers, esters, salts and solvates thereof More preferably the second active ingredient is budesonide or an epimer thereof, such as the 22R-epimer of budesonide.

The pharmaceutical compositions according to the invention can be used for the treatment or prophylaxis of a respiratory disorder, in particular the treatment or prophylaxis of asthma, rhinitis or COPD.

In a further aspect the invention provides a method of treating a respiratory disorder, in particular asthma, rhinitis or COPD, in a mammal, which comprises administering to a patient a pharmaceutical composition as herein defined.

The compositions of the invention can be inhaled from any suitable MDI device. Doses will be dependent on the severity of the disease and the type of patient, but are preferably 4.5/80 mcg or 4.5/160 mcg per actuation as defined above.

The concentration of PVP (0.001% w/w) used in this formulation has been found to give consistently stable formulations over the required dose range, incorporating a wide range of concentrations of the active components, and at a much lower concentration than indicated in the prior art.

The invention is illustrated by the following examples.

EXPERIMENTAL SECTION

Two methods can be used to evaluate physical suspension stability: Optical suspension characterisation (OSCAR), and TURBISCAN. Both methods are used to semi-quantify sedimentation/creaming rates. OSCAR measurements are performed using the PET bottles directly. For TURBISCAN analysis, the suspensions are transferred to custom designed pressure cells for measurement of light transmittance and backscattering.

Methodology

Oscar

Optical Suspension Characterisation (OSCAR) equipment is custom designed for the rapid and reproducible semi-quantification of metered dose inhaler suspension characteristics.

Figure 1:
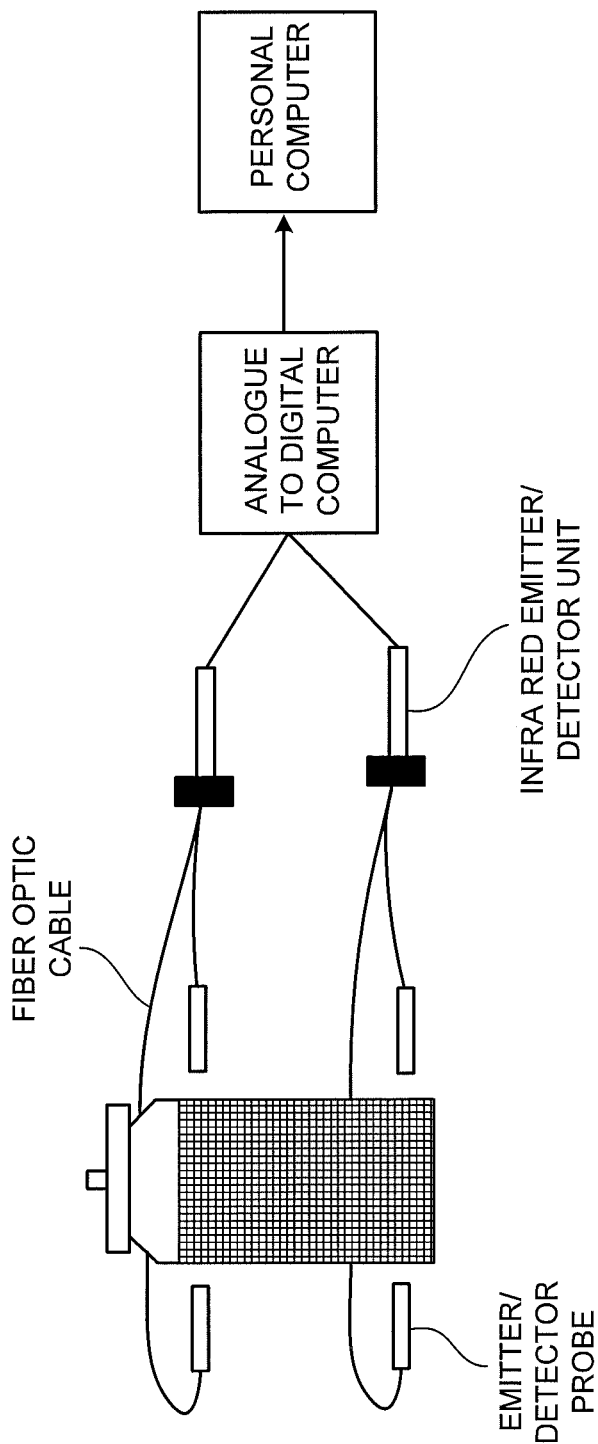
FIG. 1 is a schematic drawing of an Optical Suspension Characterisation (OSCAR) set-up.

The OSCAR equipment utilises changes in light transmission with time, to characterise a pre-agitated suspension formulation (a schematic diagram of the equipment is shown in FIG. 1). The equipment consists of a twin headed test assembly. The head on the left side of the equipment is used with dilute suspensions and the right for concentrated suspensions. The selector switch mounted between the two test heads is used to alternate concentration choice. The output from the selected test head is directed to the equipment mounted voltage display and to the computer for data logging. The analogue signals from photodetectors are digitised and the values collected in data files, these are then processed using a suitable software package. There are two equipment mounted voltage displays, one each for the upper and lower photodetectors. The upper and lower photodetectors are height adjustable and a position readout display is provided to indicate the set height for each test run.

The Reagecon Turbidity standards (2500-4000 NTU) are used to calibrate the sensitivity of the OSCAR equipment. In this case, the 3000 NTU turbidity calibration standard is used as a standard calibration check. However any of the turbidity standards can be used to adjust the sensitivity of the probes to a specific voltage appropriate to the formulation.

Samples for test on the OSCAR equipment are presented in PET bottles crimped with non-metering valves.

For background information and prior art for this method refer to papers from Drug Delivery to the Lungs IX, 1997, Method Development of the OSCAR technique for the characterization of metered dose inhaler formulations, Authors N. Govind, P. Lambert And Drug delivery to the Lungs VI, 1995, A Rapid Technique for Characterisation of the Suspension Dynamics of metered Dose Inhaler Formulations, Author, P A Jinks (3M Healthcare Ltd)

Turbiscan

Turbiscan MA 2000 is a concentrated dispersion and emulsion stability and instability analyser, or a vertical scan macroscopic analyser. It consists of a reading head moving along a flat-bottomed, 5 ml cylindrical glass cell, which takes readings of transmitted and backscattered light every 40 µm on a maximum sample height of 80mm. The scan can be repeated with a programmable frequency to obtain a macroscopic fingerprint of the sample.

The reading head uses a pulsed near infrared light source (wavelength=850 nm) and two synchronous detectors:
  Transmission detector: Picks up light transmitted through the solution in the tube, at 0°
  Backscattering detector: Receives the light back scattered by the product at 135°.

The profile obtained characterises the samples homogeneity, concentration and mean particle diameter. It allows for quantification of the physical processes the sample is undergoing. As well as detecting destabilisation, Turbiscan allows comparison of, for example, the sedimentation rate of different suspensions.

Turbiscan may be used in several modes, e.g., transmitted or backscattering modes. Turbiscan has been used here in these examples to measure the transmitted light as a function of time.

Dispersion instability is the result of two physical processes: a) particle size increases as a result of the formation of aggregates, due to flocculation; and b) particle migration resulting in creaming or sedimentation. When a product is stable (i.e., no flocculation, creaming or sedimentation), the transmitted and backscattered light will remain constant i.e. scans of these will show a constant level profile. If the product undergoes changes in particle size, variations in the transmitted/ backscattered light show as change in the direction of the scan from horizontal or steady state profile.

For pressurised systems a cell capable of handling pressurised samples is required. Such a cell was used for the evaluations of these HFA formulations. The scans were performed in the AUTO mode.

The % transmission averages shown in the figure (see later) were taken from a zone around the middle of the suspension sample.

Initial Evaluation

For the initial evaluation, only OSCAR was used.

Formulations containing formoterol fumarate dihydrate, budesonide, 0.001% w/w PVP K25 and either 0.1% w/w or 0.3% PEG 1000 in HFA-227 were prepared in polyethylene terephthalate (PET) bottles crimped with a continuous valve. For all formulations, the formoterol fumarate dihydrate concentration remained constant at 0.09 mg/ml (equivalent to 4.5 mcg formoterol fumarate dihydrate per actuation) and the budesonide concentration varied between approximately 1 mg/ml to 8 mg/ml (equivalent to 40 mcg to 320 mcg per actuation).

| Early OSCAR data for Symbicort pMDI formulations ||||||
|---|---|---|---|---|---|
| Budesonide dose ex-actuator | Formoterol dose ex-actuator | PVP K25 concentration (% w/w) | Time seconds | Transmittance (mV) Lower sensor PEG concn % w/w ||
| | | | | 0.1 | 0.3 |
| 40 µg | 4.5 µg | 0.001 | 30 seconds | | 257 |
| | | | 60 seconds | | 264 |
| 80 µg | 4.5 µg | 0.001 | 30 seconds | 202 | |
| | | | 60 seconds | 240 | |
| | | 0.002 | 30 seconds | 184 | |
| | | | 60 seconds | 185 | |
| 160 µg | 4.5 µg | 0.001 | 30 seconds | 208 | 114 |
| | | | 60 seconds | 304 | 191 |
| | | 0.002 | 30 seconds | 248 | |
| | | | 60 seconds | 327 | |
| 320 µg | 4.5 µg | 0.001 | 30 seconds | | 475 |
| | | | 60 seconds | | 570 |
| | | 0.002 | 30 seconds | | 930 |
| | | | 60 seconds | | 1443 |

OSCAR analysis of these formulations gave relatively low light transmittance values at the lower sensor, which is indicative of stable suspensions with low flocculation characteristics. Early indications were that the 0.001% w/w PVP with 0.3% PEG 1000 would give the best suspension.

FURTHER EVALUATION: various concentrations of PVP K25 with a constant PEG 1000 concentration of 0.3% w/w.

OSCAR, Turbiscan and photographic methods were used to evaluate the formulations. OSCAR and Turbiscan techniques have been described earlier. Samples with varying concentrations of PVP were analysed to determine suspension stability over time.

Photographic Analysis

For the photographic analysis, samples were prepared in PET bottles and photographed digitally over time, using a black background. These photographs (some of which are shown here) show the behaviour of the suspension over time and allow easy comparison of the effectiveness of the various concentrations of PVP. The concentration of PVP varied from 0.0001 to 0.05% w/w. From left to right on the photographs the concentration of PVP is as follows:

| 0.0001 | 0.0005 | 0.001 | 0.01 | 0.03 | 0.05 |
|---|---|---|---|---|---|
| far left | | | | | far right |

Digital Photography of Formulations Showing Degree of Dispersion Over Time

Figure 9:
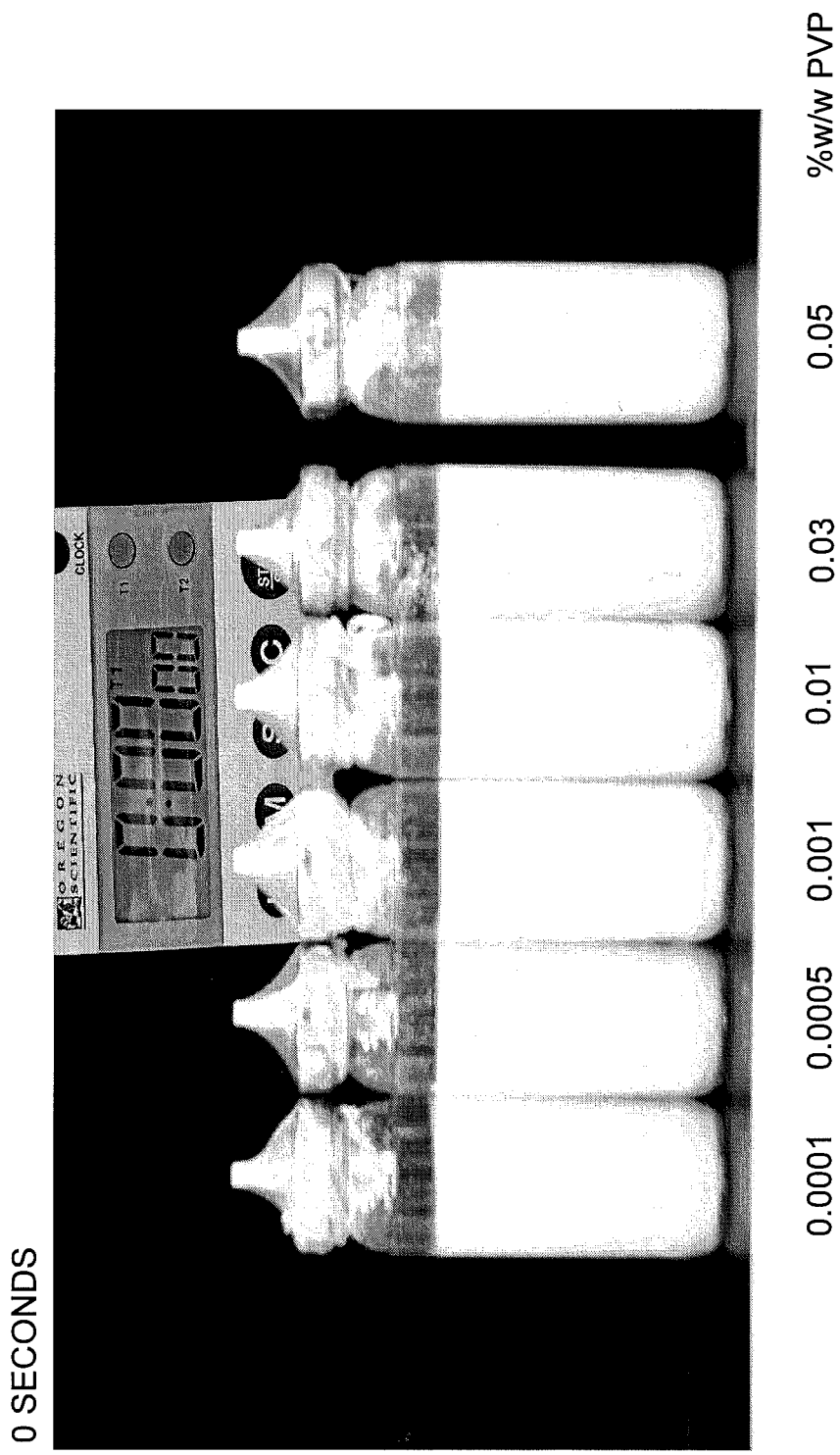
FIGS. 9-11 are a series of digital photographs, taken after standing times of 0 seconds (FIG. 9), 30 seconds (FIG. 10), and 60 seconds (FIG. 11), of suspensions in HFA 227 containing budesonide (160 µg/actuation); formoterol (4.5 µg/actuation); 0.3% PEG 1000; and PVP K25 at 0.0001%, 0.0005%, 0.001%, 0.01%, 0.03%, and 0.05% w/w.
Figure 10:
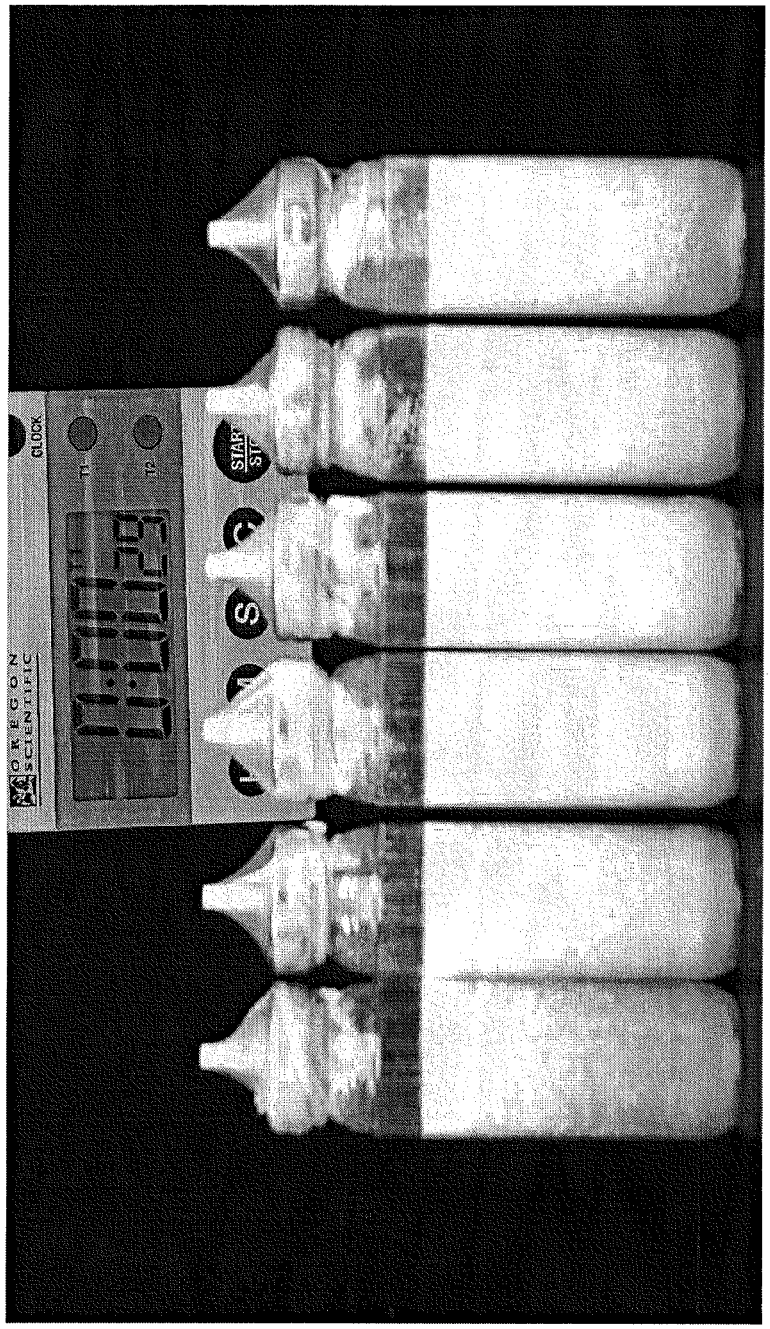
Figure 11:

FIGS. 9, 10 and 11 show Budesonide 160 μg/shot, Formoterol 4.5 μg/shot with various PVP K25 concentrations and 0.3% PEG 1000 at 0, 30, and 60 seconds standing time.

Figure 12:
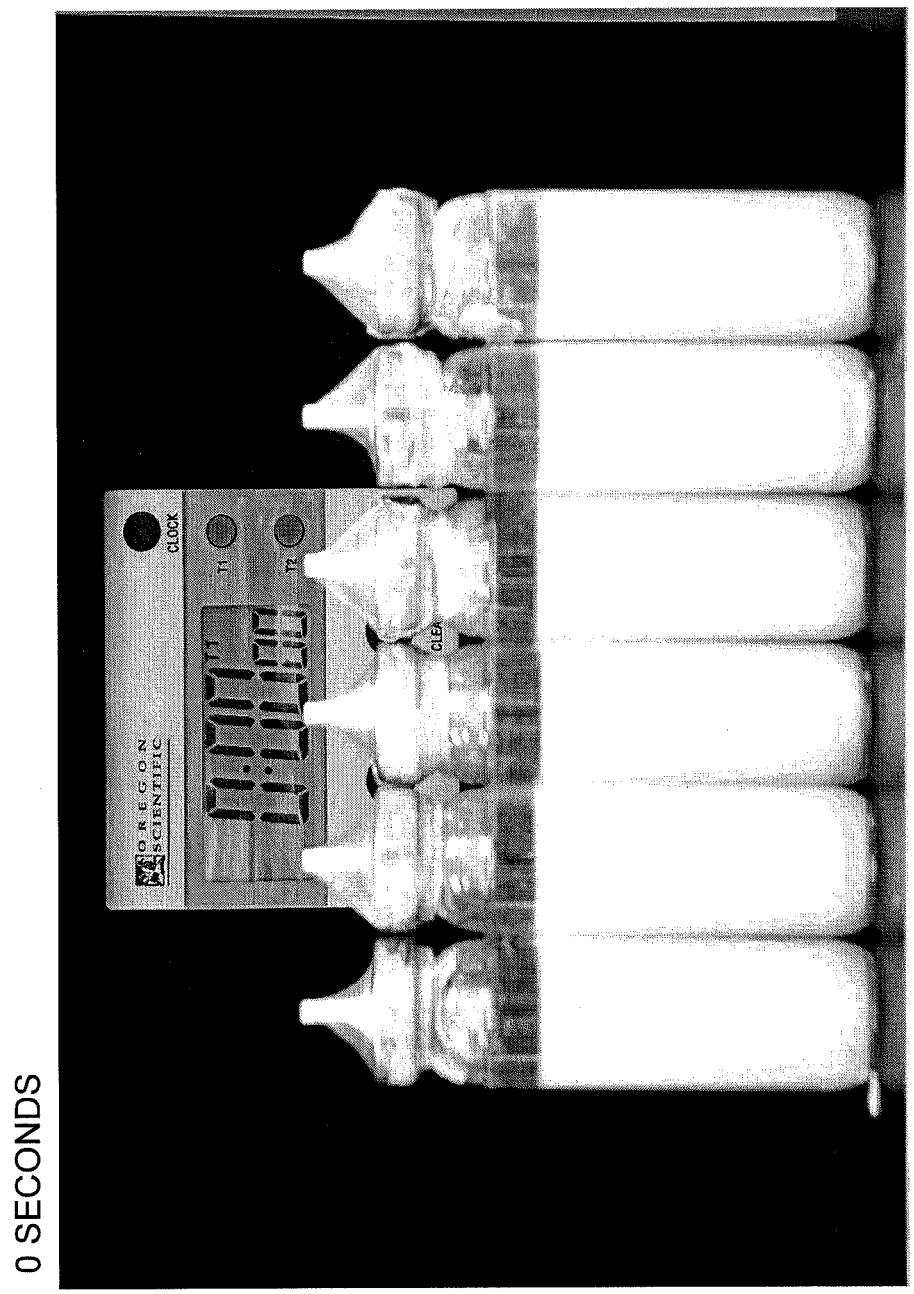
FIGS. 12-14 are a series of digital photographs, taken after standing times of 0 seconds (FIG. 12), 30 seconds (FIG. 13), and 60 seconds (FIG. 14), of suspensions in HFA 227 containing budesonide (80 µg/actuation); formoterol (4.5 µg/actuation); 0.3% PEG 1000; and PVP K25 at 0.0001%, 0.0005%, 0.001%, 0.01%, 0.03%, and 0.05% w/w.
Figure 13:
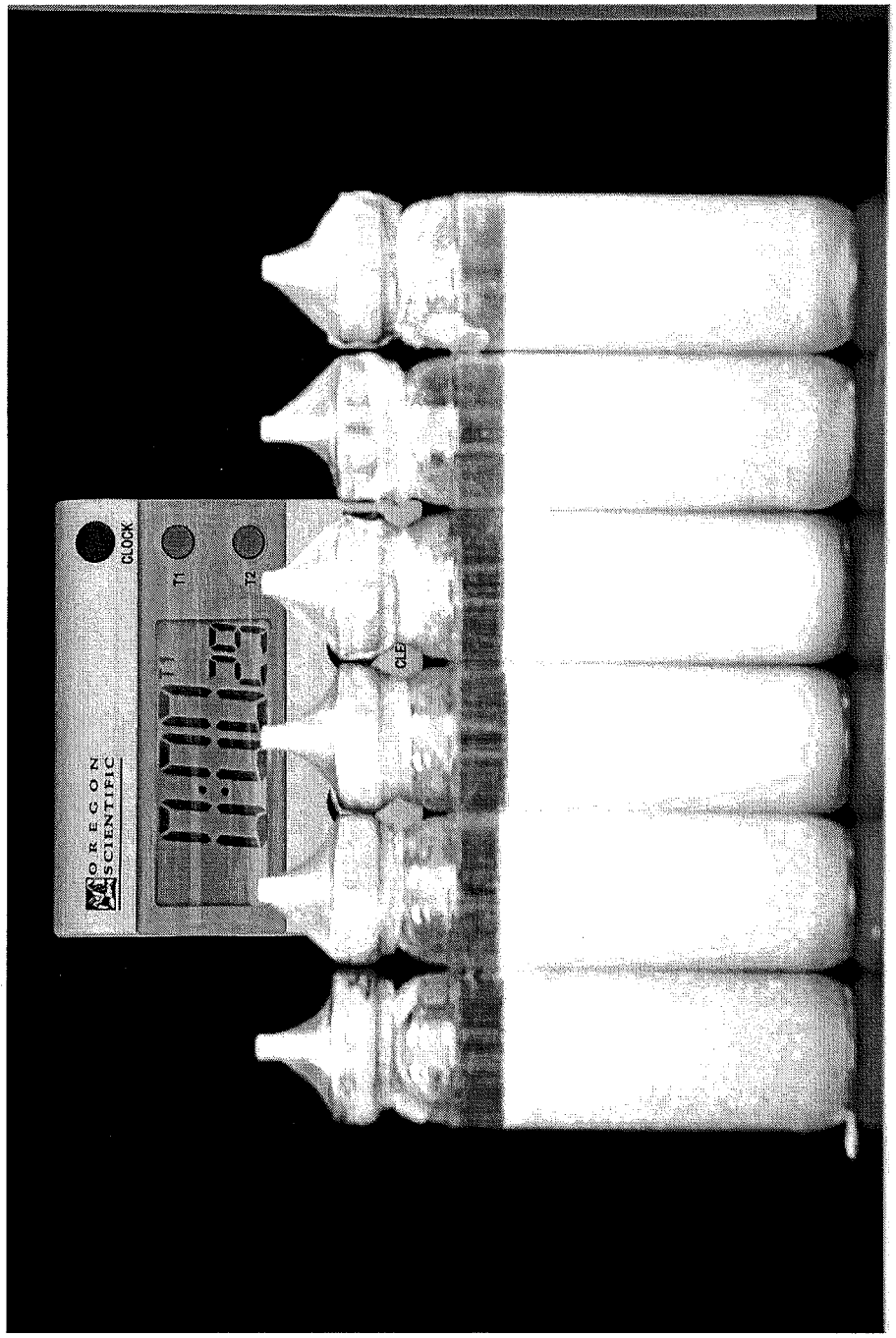
Figure 14:
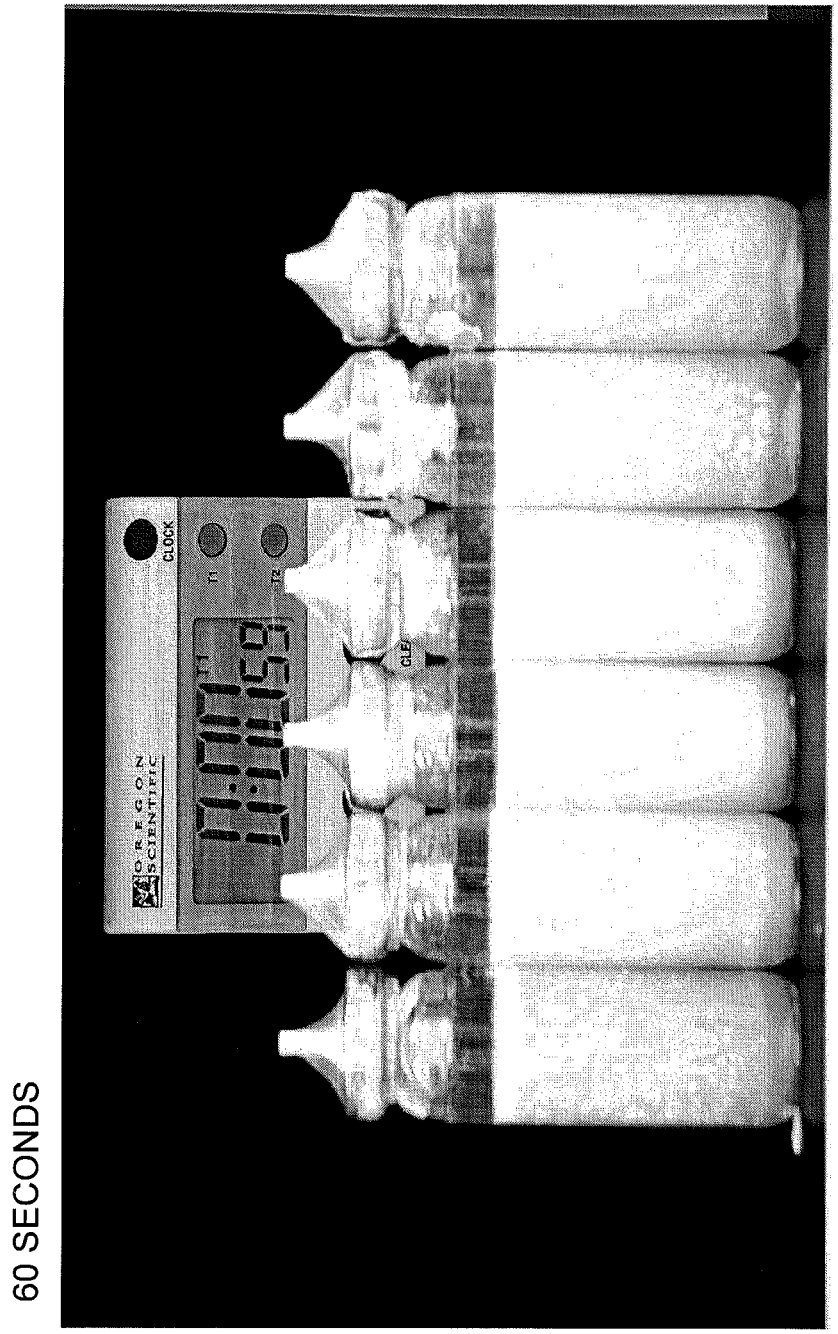

FIGS. 12, 13 and 14 shows Budesonide 80 μg/shot, Formoterol 4.5 μg/shot with various PVP K25 concentrations and 0.3% PEG 1000 at 0, 30, and 60 seconds standing time.

Table of Degree of Dispersion of Suspensions Over Time: (All Samples)

Photographs were taken of all doses (320 μg/4.5 μg to 40 μg/4.5 μg) at 0, 15, 30, 60, 90 seconds, and 2, 5 and 10 minutes. As this produced too many photographs to reproduce here, a chart has been constructed to give a representation of the degree of dispersion over time.

If the sample was fully suspended, the sample was rated 0, i.e., at 0 minutes they were fully dispersed. From there, the samples have been rated in increments of 1-5 at 20% intervals to express the degree of dispersion: i.e., 0 was fully suspended and 5 fully creamed. This allows some comparison across the whole dose range and PVP concentration range used.

(Note concentration of Formoterol is 4.5 μg/shot in all the samples)

(Samples are all fully dispersed at 0 seconds and therefore all have a score of 0)

Fully dispersed—0
More than 80% dispersed, i.e., less than 20% clear liquid present 1
More than 60% dispersed, i.e., less than 40% clear liquid present 2
Less than 40% dispersed, i.e., more than 60% clear liquid present 3
Less than 20% dispersed, i.e., more than 80% clear liquid present 4
Fully creamed 5

TABLE OF DEGREE OF DISPERSION OF SUSPENSIONS OVER TIME: ALL SAMPLES

| Dose μg/shot | Time | PVP concentration (% w/w) | | | | | |
|---|---|---|---|---|---|---|---|
| Budesonide | Sec/mins | 0.0001 | 0.0005 | 0.001 | 0.01 | 0.03 | 0.05 |
| 320 | 15 | 2 | 1 | 0-1 | 0-1 | 0-1 | 0-1 |
| | 30 | 3 | 3 | 2 | 1-2 | 2 | 2 |
| | 60 | 4 | 4 | 3-4 | 2 | 3 | 3-4 |
| | 90 | 4 | 5 | 5 | 3 | 5 | 5 |
| | 2 | 5 | 5 | 4-5 | 4-5 | 5 | 5 |
| | 5 | 5 | 5 | 5 | 5 | 5 | 5 |
| | 10 | 5 | 5 | 5 | 5 | 5 | 5 |
| 160 | 15 | 3 | 2 | 0-1 | 0-1 | 2 | 2 |
| | 30 | 3 | 2 | 1 | 1 | 2 | 2 |
| | 60 | 5 | 4 | 1 | 2 | 4 | 5 |
| | 90 | 5 | 5 | 1 | 2 | 5 | 5 |
| | 2 | 5 | 5 | 1 | 2 | 5 | 5 |
| | 5 | 5 | 5 | 2 | 4 | 5 | 5 |
| | 10 | 5 | 5 | 2 | 4 | 5 | 5 |
| 80 | 15 | 2 | 1 | 0 | 0 | 1 | 1 |
| | 30 | 3 | 2 | 1 | 1 | 2 | 2 |
| | 60 | 4 | 2 | 1 | 1-2 | 3 | 3 |
| | 90 | 5 | 3 | 1-2 | 1-2 | 4 | 3 |
| | 2 | 5 | 3-4 | 1 | 1 | 5 | 4 |
| | 5 | 5 | 4 | 2 | 2 | 5 | 5 |
| | 10 | 5 | 5 | 3 | 3 | 5 | 5 |
| 40 | 15 | 1 | 1 | 0 | 0 | 1 | 2 |
| | 30 | 2 | 1 | 1 | 2 | 2 | 3 |
| | 60 | 1-2 | 1 | 1 | 2 | 2 | 3 |
| | 90 | 1-2 | 1-2 | 1-2 | 2 | 2-3 | 4 |
| | 2 | 2 | 2 | 2 | 3 | 4 | 5 |
| | 5 | 3 | 2 | 2 | 3 | 4 | 5 |
| | 10 | 4-5 | 3 | 2 | 4 | 5 | 5 |

Suspensions considered excellent are highlighted in bold.

It can be seen that the formulations with 0.001% w/w PVP gave the best suspension stability overall.

OSCAR DATA (Graphs of Light Transmission Versus Time)

Figure 2:
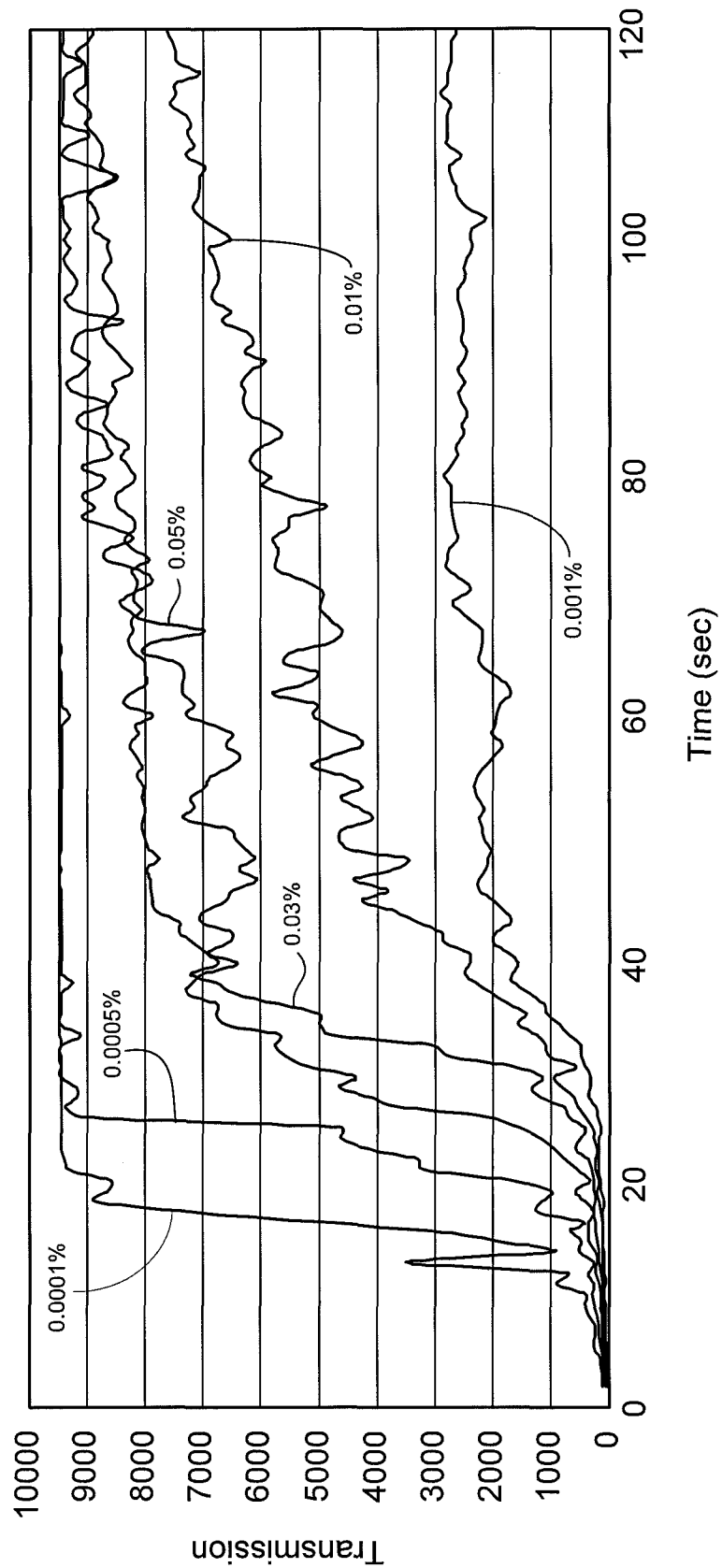
FIGS. 2-3 are graphs showing the averages of OSCAR data (lower sensor) for formulations in HFA 227 containing 4.5 µg formoterol; 0.3% w/w PEG 1000; 0.0001% -0.05% w/w PVP K25; and 160 µg budesonide (FIG. 2) or 80 µg budesonide (FIG. 3).

FIG. 2 shows the average OSCAR transmission readings (lower sensor only) for various concentrations of PVP K25. A low transmission reading indicates that the suspension is dispersed, preventing light being transmitted. Hence, it can be seen that the lowest line is the most stable formulation. This is the 0.001% PVP sample.

Figure 3:
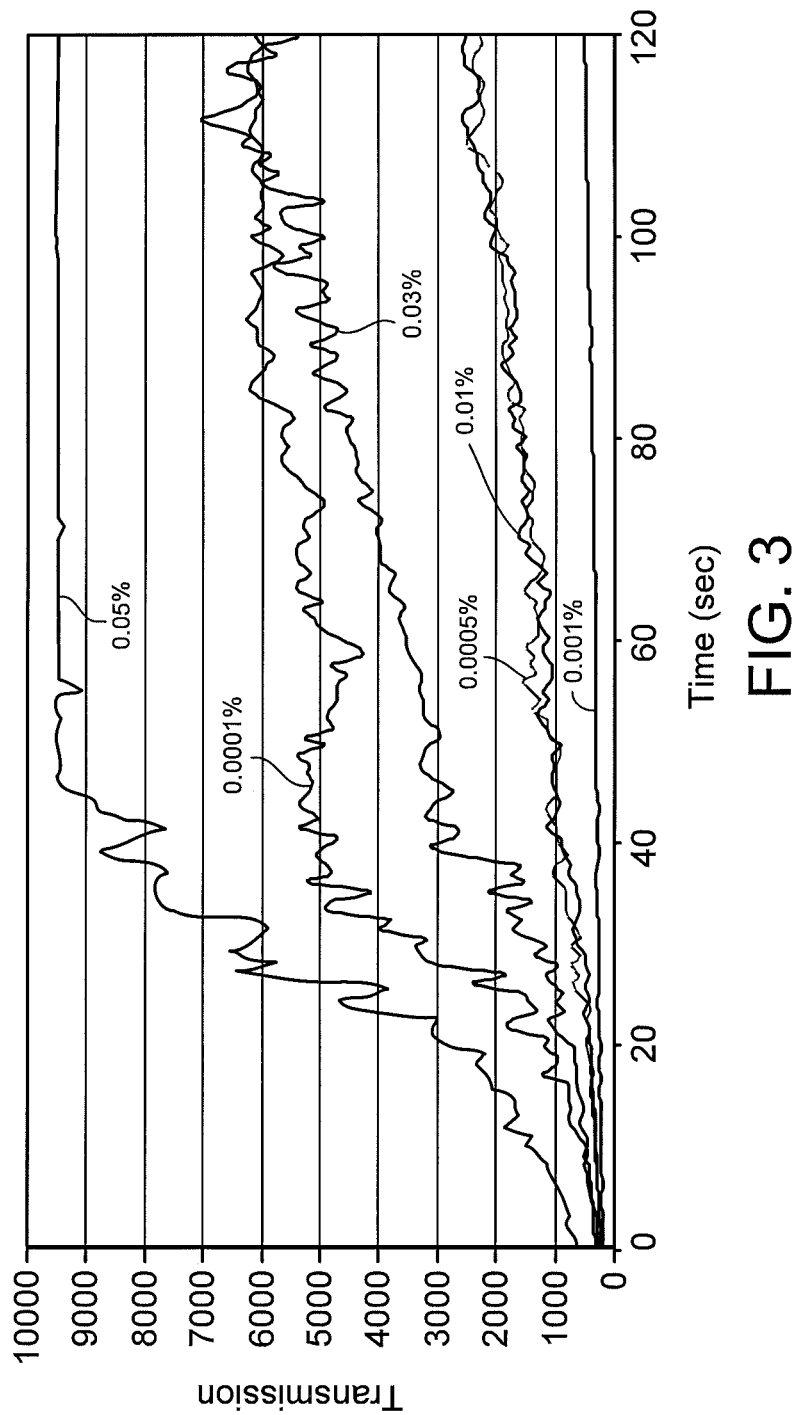
Figure 4:
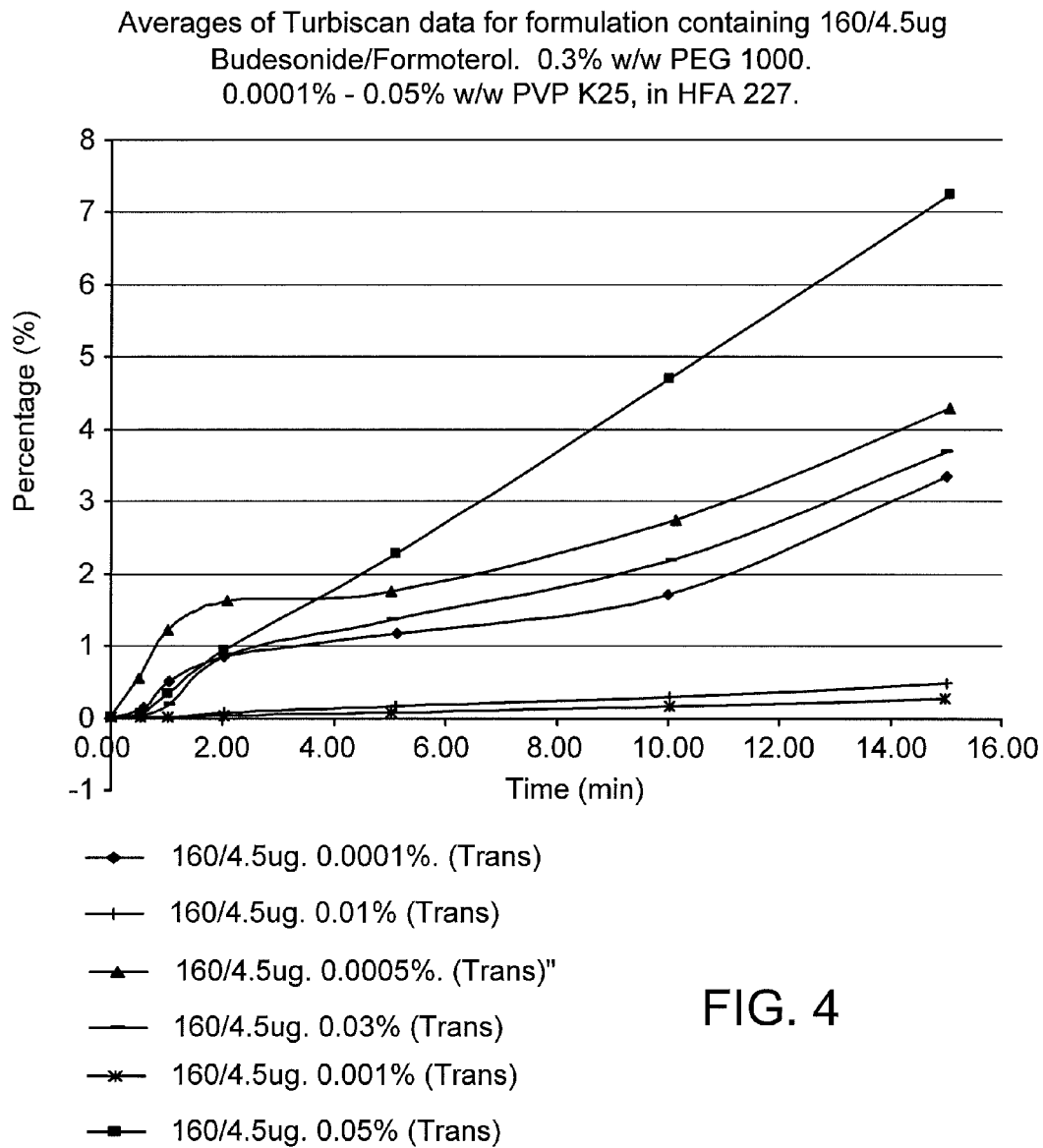
FIGS. 4-6 are graphs showing the averages of Turbiscan data for formulations in HFA 227 containing 4.5 µg formoterol; 0.3% w/w PEG 1000; 0.0001% -0.05% w/w PVP K25; and 160 µg budesonide (FIG. 4), 80 µg budesonide (FIG. 5), or 40 µg budesonide (FIG. 6).
Figure 5:
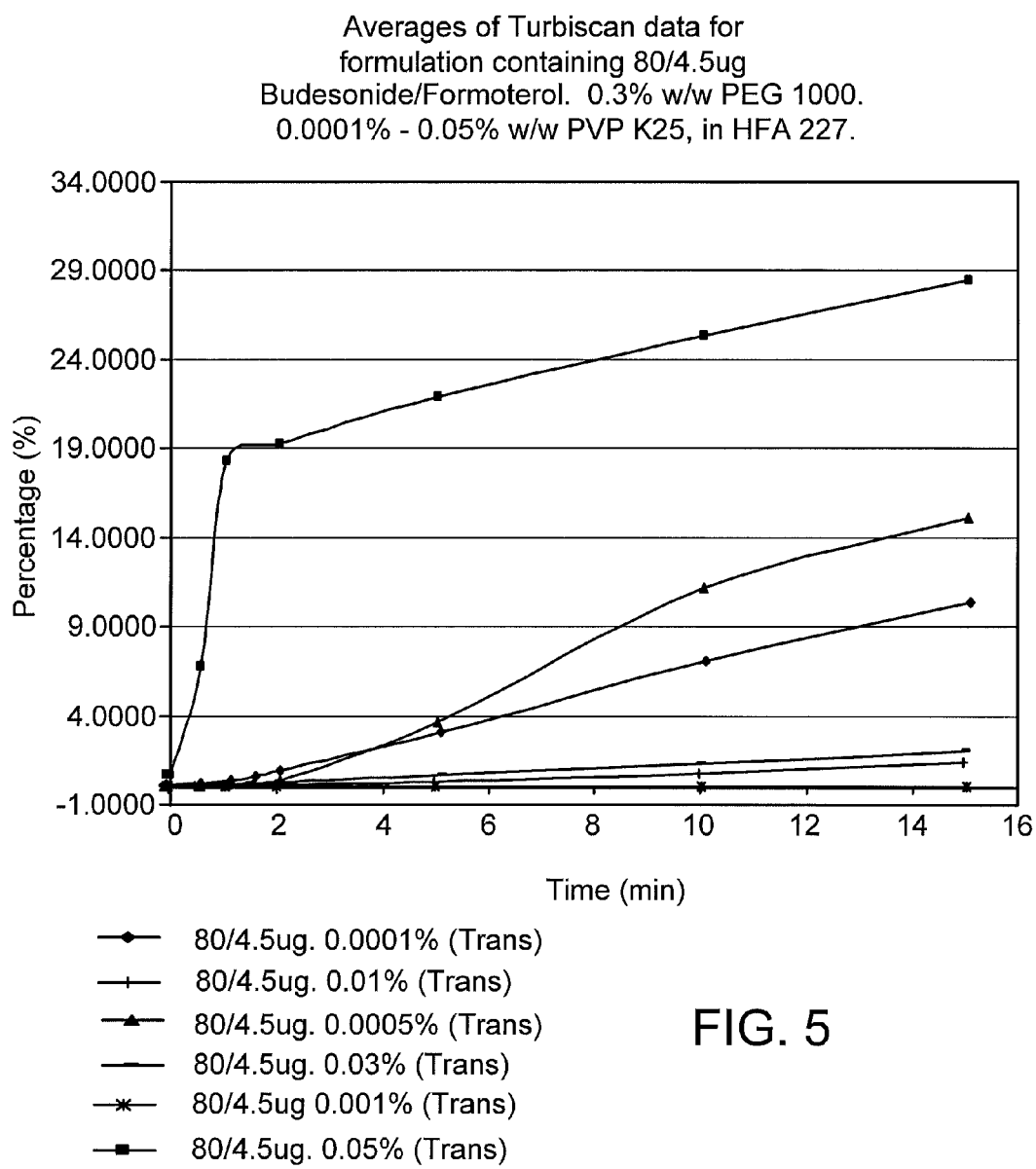
Figure 6:
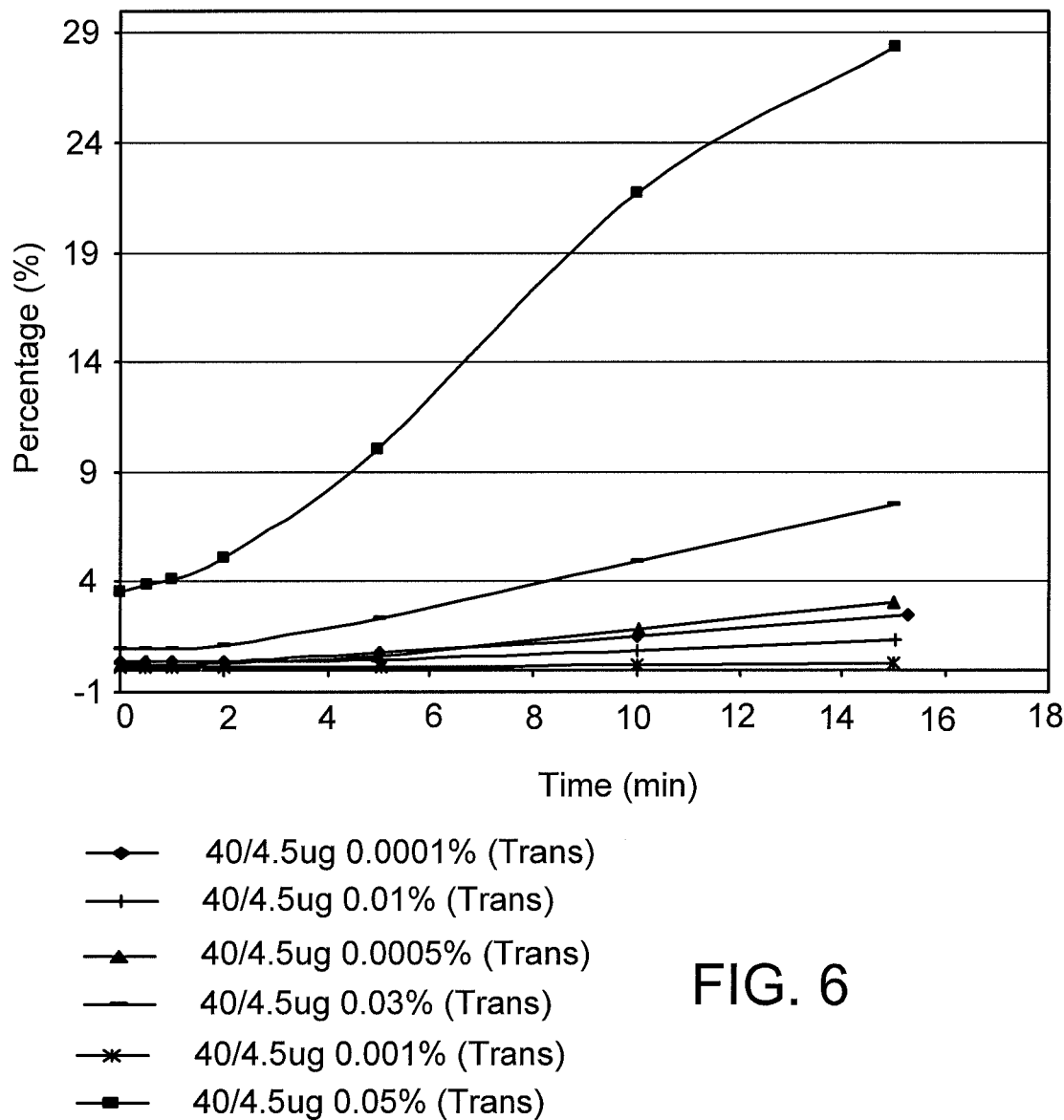

In FIG. 3, the bottom line, again with low the load cell located at the top of the upper crosshead. This program was designed to output the return force at 0.5mm stem return as this is the point at which the metering chamber is considered to refill. A low return force is indicative of high friction and potential sticking problems. It also suggests there may be a problem with low actuation weights as the propellant enters the metering chamber more slowly and has time to vaporise. Force to fire testing was performed at preset actuations.

Data

Force to Fire Data

Figure 7:
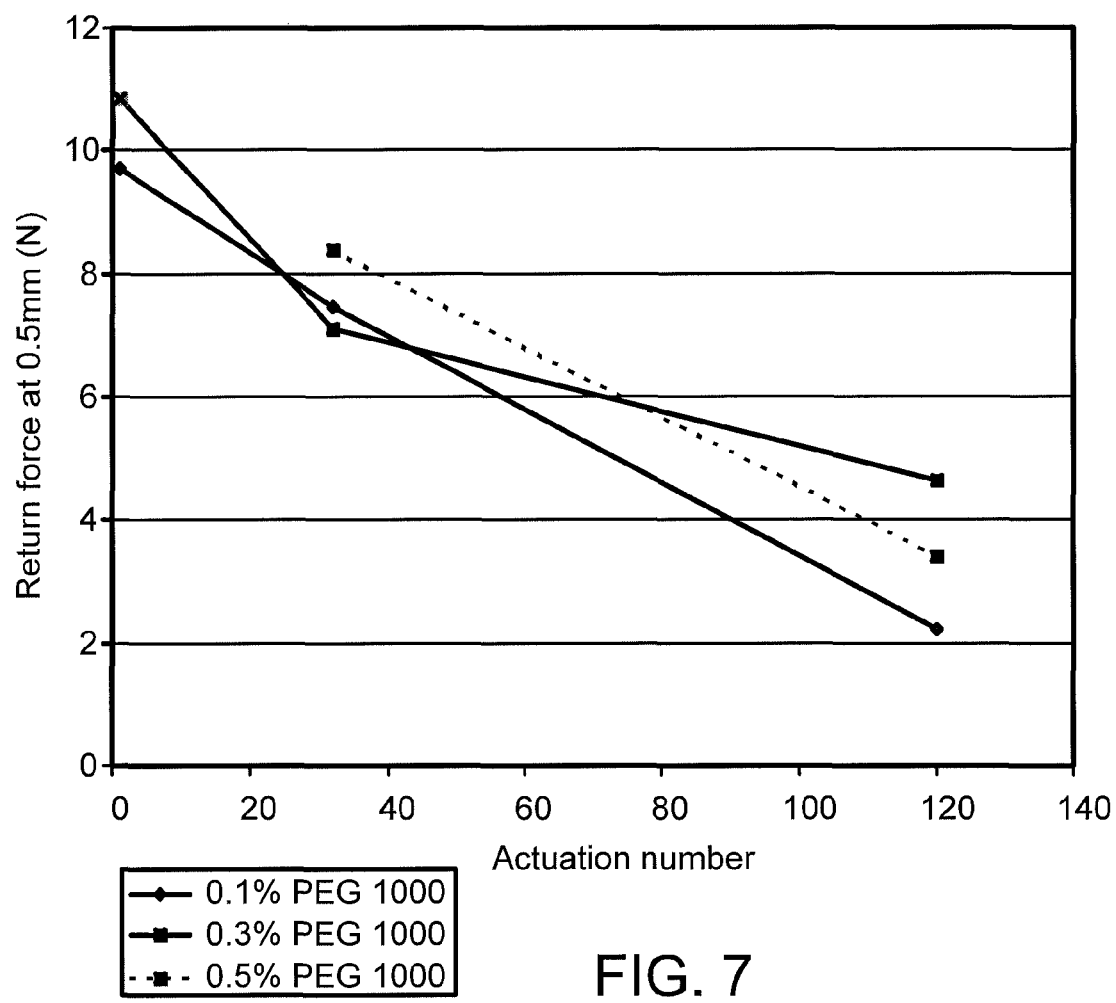
FIG. 7 is a graph showing the effect of PEG 1000 concentration on stem return force for formulations containing 4.5 µg formoterol; 160 µg budesonide; and 0.1%, 0.3%, or 0.5% w/w PEG 1000.

FIG. 7 shows the effect of PEG 1000 concentration on stem return force for the 4.5/160 µg formoterol/budesonide formulation This shows that at 120 actuations, the return force is greater for the 0.3% w/w PEG 1000 concentration than for the other concentrations of 0.5% and 0.1%. In general, the higher the return force the lesser the chance of the valve stem sticking. The above data shows that in this case 0.3% would be preferred.

Turbiscan Data

Figure 8:
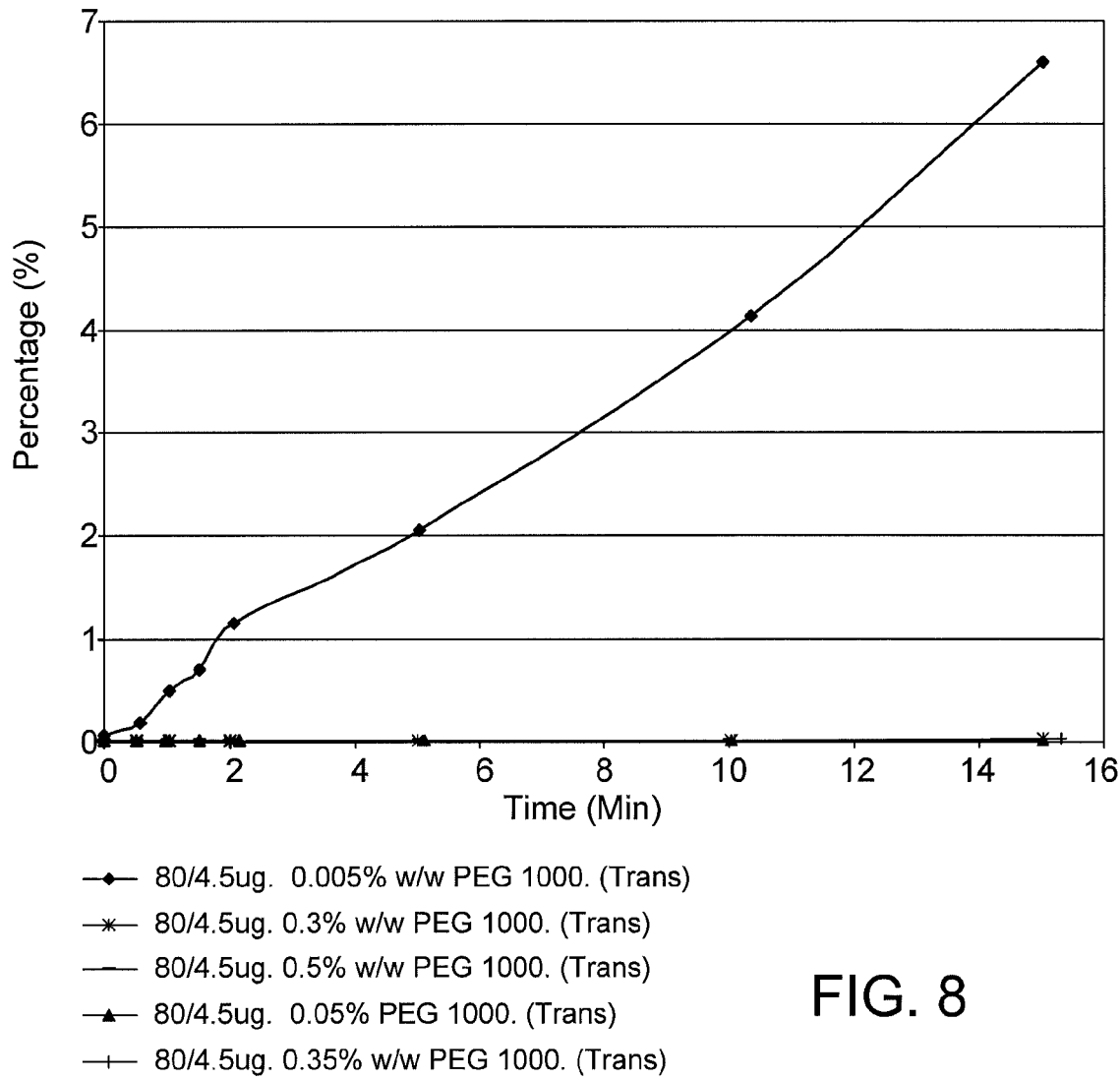
FIG. 8 is a graph showing the averages of Turbiscan data for formulations in HFA 227 containing 80 µg budesonide; 4.5 µg formoterol; 0.0001% PVP K25; and 0.005% - 0.5% w/w PEG 1000.

The Turbiscan data (FIG. 8) shows that there is little difference between the stability of suspensions made with varying levels of PEG 1000 except for the 0.005% w/w level which was unsatisfactory.

Photographic Analysis

Digital photographs of suspensions containing Budesonide, Formoterol, HFA 227, 0.001% w/w PVP and varying levels of PEG 1000 show little variation in suspension stability over time (0 seconds to 10 minutes) except for the 0.005% w/w PEG level (in agreement with the Turbiscan data).

Figure 15:
FIGS. 15-16 are digital photographs, taken after standing times of 0 minutes (FIG. 15) and 10 minutes (FIG. 16), of suspensions in HFA 227 containing budesonide (80 µg/actuation); formoterol (4.5 µg/actuation); 0.001% PVP K25; and PEG 1000 at 0.005, 0.05, 0.35, and 0.5% w/w.
Figure 16:

FIGS. 15 and 16 show Budesonide 80 µg/shot, Formoterol 4.5 µg/shot with 0.001% PVP K25 and various concentrations of PEG 1000 at 0 (1) and 10 minutes (2) standing time.

Product Performance Data

In addition to the above, product performance data for formulations containing formoterol fumarate dihydrate/budesonide at the following strengths: 4.5/80 mcg per actuation and 4.5/160 mcg per actuation, with 0.001% PVP K25 and either 0.1% or 0.3% PEG 1000, were stable for up to 12 months at 25° C./60% RH.

Product performance data for Symbicort formulations containing 0.001% PVP K25 and 0.1% PEG 1000 in HFA-227

| Product strength (µg) (FFD/budesonide) | Drug | Initial | Fine particle fraction (% cumulative undersize for 4.7 µm cut-off) | |
|---|---|---|---|---|
| | | | 25° C./60% RH 6 months | 25° C./60% RH 12 months |
| 4.5/80 | Budesonide | 51.3 | 52.8 | 62.0 |
| | FFD | 55.4 | 53.5 | 59.7 |
| 4.5/160 | Budesonide | 50.0 | 48.8 | 47.0 |
| | FFD | 54.2 | 52.1 | 51.3 |

Product performance data for Symbicort formulations containing 0.001% PVP K25 and 0.3% PEG 1000 in HFA-227

| Product strength (µg) (FFD/budesonide) | Drug | Initial | Fine particle fraction (% cumulative undersize for 4.7 µm cut-off) | |
|---|---|---|---|---|
| | | | 25° C./60% RH 6 months | 25° C./60% RH 12 months |
| 4.5/80 | Budesonide | 55.8 | 50.6 | 51.3 |
| | FFD | 64.2 | 57.6 | 58.7 |
| 4.5/160 | Budesonide | 48.7 | 50.2 | 52.3 |
| | FFD | 55.6 | 59.1 | 61.2 |

The invention claimed is:

1. A pharmaceutical suspension composition comprising formoterol fumarate dihydrate; budesonide; 1,1,1,2,3,3,3-heptafluoropropane (HFA227); polyvinyl pyrrolidone (PVP); and polyethylene glycol (PEG), wherein the budesonide is present in the composition at a concentration in the range of 1 mg/ml to 8 mg/ml, the PVP is present at a concentration in the range of 0.001% to 0.01% w/w, and the PEG is present at a concentration in the range of 0.05 to 0.5% w/w.

2. The pharmaceutical suspension composition of claim 1, wherein the PEG is PEG 1000 (PEG with an average molecular weight of 1,000).

3. The pharmaceutical suspension composition of claim 1, wherein the PVP is PVP K25 (PVP with a nominal K-value of 25).

4. The pharmaceutical suspension composition of claim 1, wherein the PVP is present in the composition at a concentration of 0.001% w/w.

5. The pharmaceutical suspension composition of claim 4, wherein the PVP is PVP K25.

6. The pharmaceutical suspension composition of claim 5, wherein the PEG is PEG 1000.

7. The pharmaceutical suspension composition of claim 1, wherein the budesonide is in the form of its 22R-epimer.

8. The pharmaceutical suspension composition of claim 1, wherein the formoterol fumarate dihydrate is in the form of its R,R enantiomer.

9. A pharmaceutical suspension composition comprising formoterol fumarate dihydrate, budesonide, HFA227, PVP K25, and PEG-1000, wherein the budesonide is present at a concentration in the range of 1 mg/ml to 8 mg/ml and the PVP K25 is present at a concentration of 0.001% w/w.

10. The pharmaceutical suspension composition of claim 9, wherein the PEG-1000 is present at a concentration of 0.3% w/w.

11. The pharmaceutical suspension composition of claim 9, wherein the budesonide is in the form of its 22R-epimer.

12. The pharmaceutical suspension composition of claim 9, wherein the formoterol fumarate dihydrate is in the form of its R,R enantiomer.

13. A method of treating a respiratory disorder, the method comprising administering the pharmaceutical suspension composition of claim 1 to a patient identified as in need of treatment with the composition.

14. The method of claim 13, wherein the patient is suffering from asthma.

15. The method of claim 13, wherein the patient is suffering from chronic obstructive pulmonary disease (COPD).

16. A method of treating a respiratory disorder, the method comprising administering the pharmaceutical suspension composition of claim 9 to a patient identified as in need of treatment with the composition.

17. The method of claim 16, wherein the patient is suffering from asthma.

18. The method of claim 16, wherein the patient is suffering from COPD.

19. A method of treating a respiratory disorder, the method comprising administering the pharmaceutical suspension composition of claim 10 to a patient identified as in need of treatment with the composition.

20. The method of claim 19, wherein the patient is suffering from asthma.

21. The method of claim 19, wherein the patient is suffering from COPD.

22. A pressurized metered dose inhaler containing the pharmaceutical suspension composition of claim 1.

23. The inhaler of claim 22, wherein the PEG is PEG 1000.

24. The inhaler of claim 22, wherein the PVP is PVP K25.

25. The inhaler of claim 22, wherein the PVP is present in the composition at a concentration of 0.001% w/w.

26. The inhaler of claim 25, wherein the PVP is PVP K25.

27. The inhaler of claim 26, wherein the PEG is PEG 1000.

28. A pressurized metered dose inhaler containing the pharmaceutical suspension composition of claim 9.

29. A pressurized metered dose inhaler containing the pharmaceutical suspension composition of claim 10.

30. A method of treating a respiratory disorder, the method comprising
    providing the inhaler of claim 22 to a patient in identified need thereof; and
    causing the patient to inhale the composition from the inhaler.

31. The method of claim 30, wherein the patient is suffering from asthma.

32. The method of claim 30, wherein the patient is suffering from COPD.

33. A method of treating a respiratory disorder, the method comprising
    providing the inhaler of claim 22; and
    instructing a patient in need thereof to inhale the composition from the inhaler.

34. The method of claim 33, wherein the patient is suffering from asthma.

35. The method of claim 33, wherein the patient is suffering from COPD.

36. A method of treating a respiratory disorder, the method comprising
    providing the inhaler of claim 26 to a patient in identified need thereof; and
    causing the patient to inhale the composition from the inhaler.

37. The method of claim 36, wherein the patient is suffering from asthma.

38. The method of claim 36, wherein the patient is suffering from COPD.

39. A method of treating a respiratory disorder, the method comprising
    providing the inhaler of claim 26; and
    instructing a patient in need thereof to inhale the composition from the inhaler.

40. The method of claim 39, wherein the patient is suffering from asthma.

41. The method of claim 39, wherein the patient is suffering from COPD.

42. A method of treating a respiratory disorder, the method comprising
    providing the inhaler of claim 28 to a patient in identified need thereof; and
    causing the patient to inhale the composition from the inhaler.

43. The method of claim 42, wherein the patient is suffering from asthma.

44. The method of claim 42, wherein the patient is suffering from COPD.

45. A method treating a respiratory disorder, the method comprising
    providing the inhaler of claim 28; and
    instructing a patient in need thereof to inhale the composition from the inhaler.

46. The method of claim 45, wherein the patient is suffering from asthma.

47. The method of claim 45, wherein the patient is suffering from COPD.

48. A method of treating a respiratory disorder, the method comprising
    providing the inhaler of claim 29 to a patient in identified need thereof; and
    causing the patient to inhale the composition from the inhaler.

49. The method of claim 48, wherein the patient is suffering from asthma.

50. The method of claim 48, wherein the patient is suffering from COPD.

51. A method treating a respiratory disorder, the method comprising
    providing the inhaler of claim 29; and
    instructing a patient in need thereof to inhale the composition from the inhaler.

52. The method of claim 51, wherein the patient is suffering from asthma.

53. The method of claim 51, wherein the patient is suffering from COPD.

\* \* \* \* \*